(12) United States Patent
Wu

(10) Patent No.: US 11,179,523 B2
(45) Date of Patent: Nov. 23, 2021

(54) SMART INJECTOR

(71) Applicant: Biogen MA Inc., Cambridge, MA (US)

(72) Inventor: Haiming Wu, Weston, MA (US)

(73) Assignee: BIOGEN MA, INC., Cambridge, MA (US)

( * ) Notice: Subject to any disclaimer, the term of this patent is extended or adjusted under 35 U.S.C. 154(b) by 189 days.

(21) Appl. No.: 16/478,617

(22) PCT Filed: Jan. 19, 2018

(86) PCT No.: PCT/US2018/014387
§ 371 (c)(1),
(2) Date: Jul. 17, 2019

(87) PCT Pub. No.: WO2018/136717
PCT Pub. Date: Jul. 26, 2018

(65) Prior Publication Data
US 2020/0046908 A1 Feb. 13, 2020

Related U.S. Application Data

(60) Provisional application No. 62/448,565, filed on Jan. 20, 2017.

(51) Int. Cl.
A61M 5/315 (2006.01)
A61M 5/31 (2006.01)

(52) U.S. Cl.
CPC .... A61M 5/31568 (2013.01); A61M 5/31505 (2013.01); A61M 5/31546 (2013.01); A61M 2005/3143 (2013.01); A61M 2205/18 (2013.01)

(58) Field of Classification Search
CPC .......... A61M 5/31546; A61M 5/31568; A61M 5/31545
See application file for complete search history.

(56) References Cited

U.S. PATENT DOCUMENTS

2007/0073228 A1    3/2007  Mernoe et al.
2012/0015336 A1    1/2012  Mach
2015/0209505 A1*   7/2015  Hanson ............... A61M 5/1452
                                                          604/135

FOREIGN PATENT DOCUMENTS

EP        3028727 A1      6/2016
WO    WO 2016/140853 A1   9/2016

OTHER PUBLICATIONS

International Preliminary Report on Patentability for International Application No. PCT/US2018/014387 dated Aug. 1, 2019.

* cited by examiner

Primary Examiner — Deanna K Hall
(74) Attorney, Agent, or Firm — Finnegan, Henderson, Farabow, Garrett & Dunner LLP

(57) ABSTRACT

A device that regulates, monitors, and provides data on the progress of a large-volume injector during its injection sequence. The device comprises an injector and a monitor assembly. The injector has a syringe having a plunger, and a biasing device that biases the plunger through the syringe. The monitor assembly comprises a resistance unit configured to resist movement of the plunger, a gear connected to the plunger by the resistance unit, and a control unit configured to monitor the position, and regulate the rotation, of the gear. Wherein linear movement of the plunger causes the gear to rotate so that the control unit generates information on the position of the plunger.

20 Claims, 4 Drawing Sheets

SMART INJECTOR

This application is a national stage application under 35 U.S.C. § 371 of international application number PCT/US2018/014387, filed Jan. 19, 2018, which designated the U.S. and claims the benefit of priority of U.S. Provisional Application No. 62/448,565, filed Jan. 20, 2017, which are incorporated herein by reference.

BACKGROUND

Field

The present disclosure relates to devices for regulating, monitoring, and providing data on the administration, injection, and/or delivery of substances to a patient. More particularly, and without limitation, the disclosed embodiments relate to regulating and monitoring the administration of medication by a large-volume injector during its injection sequence.

Description of Related Prior Art

Large-volume injectors and/or drug infusers are delivery devices that facilitate the hypodermic administration of a predetermined dosage of medication. In contrast to an auto-injector, for example, which provides for the immediate administration of medication, a large-volume injector administers larger amounts of medication over a longer period of time. Often times, a patient's therapeutic regimen calls for periodic, for example, daily or weekly administrations of medication using large-volume injectors. And such regimens, because of, for example, the medication's viscosity, may require relatively slow, measured administration that may take up to approximately an hour to complete.

Although known in the art, traditional mechanical large-volume injectors suffer from the drawback of lacking smart features, such as the ability to monitor injection progression, wireless communication, and injection control. Because of this, current large-volume injectors are incapable of providing meaningful, accurate information regarding the progress of the injection. For example, current large-volume injectors cannot monitor and provide data on what amount of medication has been administered at a given time during the injection sequence, the time remaining before an injection is complete, or whether the injection has inadvertently stopped because of, for example, a blockage and/or an occlusion at the injection site. Uncertainty resulting from the lack of information about injection progress may also lead to patient discomfort. Indeed, a patient may experience anxiety while waiting for a relatively slow injection to reach its completion; especially, when there is little indication of its progress. User anxiety resulting from a lack of information about the injection progress may also lead to user error, such as, for example, premature removal of the injector before the entire dosage is delivered. Further, current large-volume injectors suffer from an inability to pause or stop an injection sequence after its initiation.

Furthermore, in traditional mechanical large-volume injectors, attempts to regulate the injection rate are typically carried out by a rigid link connecting the plunger to some other portion of the injector. Rigid links suffer from an inability to flex, which limits their positioning and adaptability within the injector. Inflexible rigid links are costly and also require more room for operation, which often leads to a bulky, obtrusive design.

SUMMARY

The present disclosure seeks to overcome the abovementioned problems. Accordingly, the disclosed embodiments include devices that regulate, monitor, and provide data on the progress of a large-volume injector during its injection sequence. As will be explained, there are several benefits of monitoring the progress of a large-volume injector.

At least one object of the disclosure is to provide a monitoring device capable of tracking the progress of an injection by accurately monitoring the position of the stopper throughout the injection sequence. Such real-time monitoring has the additional benefit of providing a patient or medical professional with assurance that the injection is proceeding without obstruction or delay. Thus, at least one object of the present disclosure is to provide a psychological benefit to the patient and medical professionals using large-volume injectors. The present disclosure also provides a physiological benefit when regulating the injection rate because a hurried injection may cause a bolus, painful bruising, or lumps to arise, which may be avoided. Further, the small footprint of the monitoring device does not require reconstruction or expansion of traditional large-volume injectors. This is due in part to a resistance unit that includes a soft link, whose flexibility allows for adaptable positioning, low cost manufacture, and controlled, regulated movement. Thus, the monitor can be used as an add-on feature to existing large-volume injectors. Yet further, instead of using optoelectrical sensors in conjunction with a large-volume injector, the mechanical nature of the present disclosure reduces the effect that may result from a drug substance's reaction to light.

For example, exemplary embodiments of the disclosure control and/or regulate the rate of injection. Controlling the rate of injection includes pausing the injection for a period of time or stopping it entirely. In this way, the monitoring device provides the benefit of allowing for partial or sequential dosing, which many therapies call for. Yet further, illustrative embodiments of the disclosure detect obstructions or occlusions at or near the injection site. According to some exemplary embodiments, alerts and/or reminders are provided regarding an inadvertent stopping of the injection caused by, for example, the presence of an obstruction or occlusion. Additionally, an alert and/or reminder may signal the occurrence of events on an injection schedule.

Accordingly, in illustrative embodiments, a device for regulating and monitoring an injection sequence of an injector is provided comprising an injector and a monitor assembly. The injector may optionally comprise a syringe having a plunger and a needle, but the plunger can also feed contents of the syringe into a non-needle delivery mechanism. The injector further comprises a biasing device that biases the plunger towards an end of the syringe. The monitor assembly comprises a resistance unit configured to resist movement of the plunger, a gear connected to the plunger by the resistance unit, and a control unit configured to rotate with, monitor the position, and regulate the rotation of the gear. The resistance unit comprises a soft link connecting the plunger to the gear, wherein linear movement of the plunger causes the gear to rotate so that the control unit generates information on the position of the plunger. The soft link allows the resistance unit to have a compact design and regulate the speed of the injection. In this way, the progress of the injection is capable of being regulated and monitored.

Other embodiments of this disclosure are disclosed in the accompanying drawings, description, and claims. Thus, this summary is exemplary only, and is not to be considered restrictive.

BRIEF DESCRIPTION OF DRAWINGS

The accompanying drawings, which are incorporated in and constitute part of this specification, and together with the description, illustrate and serve to explain the principles of various exemplary embodiments.

DETAILED DESCRIPTION OF EXEMPLARY EMBODIMENTS

Figure 1:
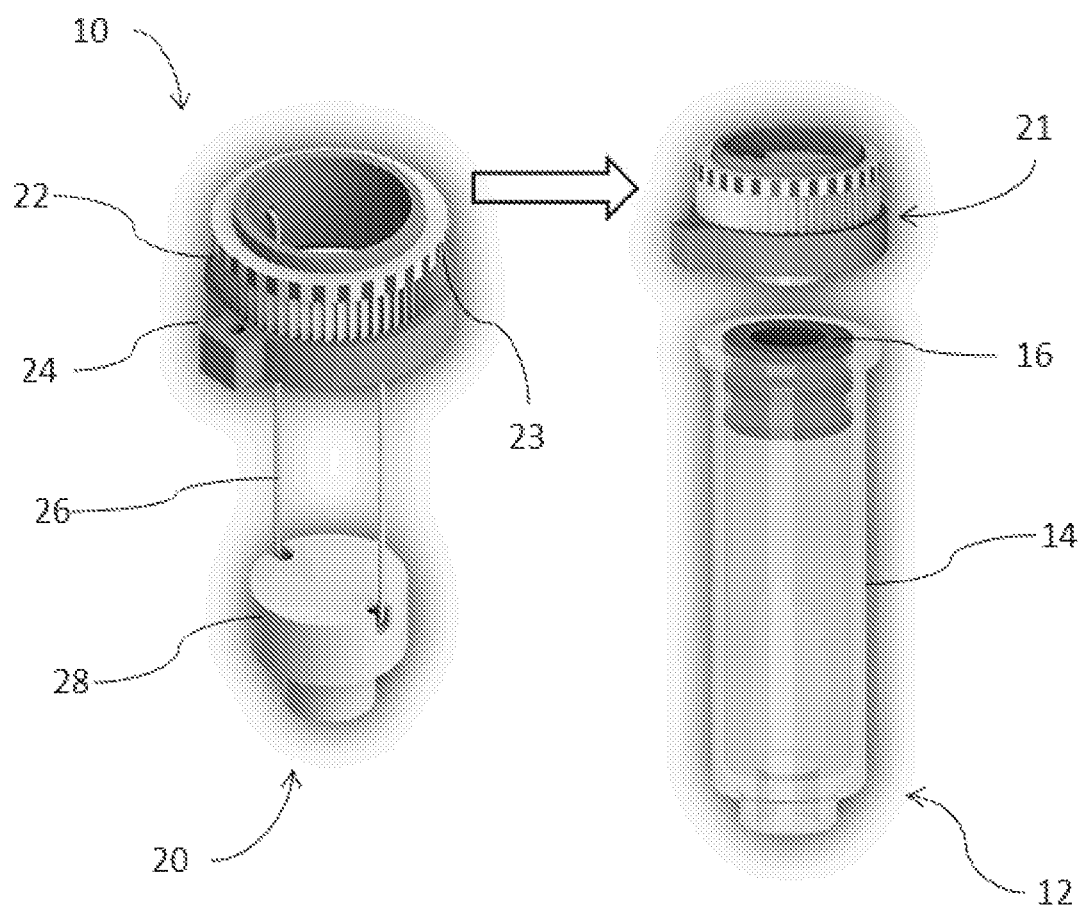
FIG. 1 depicts an exemplary device, monitory assembly, injector, and a resistance unit.
Figure 2:
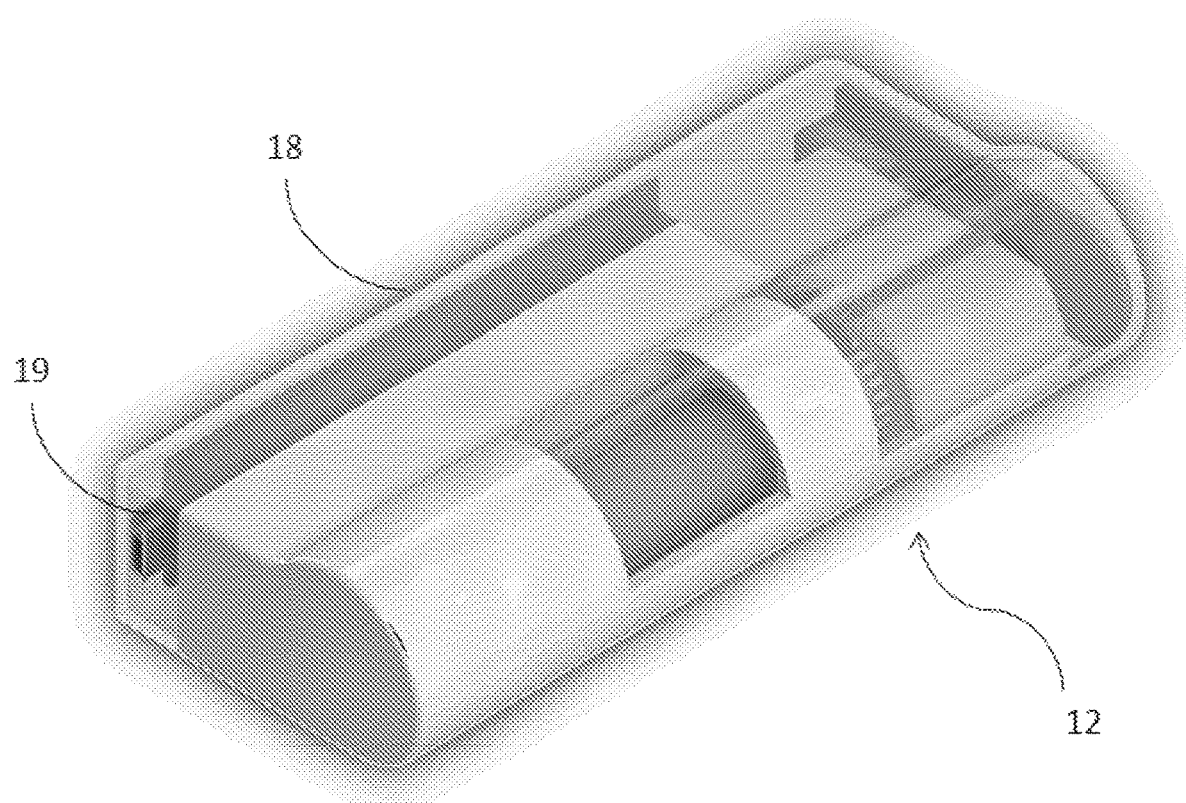
FIG. 2 depicts an exemplary embodiment of the injector.

The claimed subject matter is described with reference to the drawings, wherein like reference numerals are used to refer to like elements throughout. In the following description, for purposes of explanation, numerous specific details are set forth in order to provide a thorough understanding of the subject innovation. It may be evident, however, that the claimed subject matter may be practiced without these specific details. In other instances, well-known structures and devices are shown in block diagram form in order to facilitate describing the subject innovation. Moreover, it is to be appreciated that the drawings may not be to scale. Moreover, the words "exemplary" or "illustrative" are used herein to mean serving as an example, instance, or illustration. Any aspect or design described herein as "exemplary" or "illustrative" is not necessarily to be construed as preferred or advantageous over other aspects or designs.

According to an illustrative embodiment of the disclosure depicted in FIG. 1, device 10 for monitoring and regulating the progress of an injection is provided. The device 10 comprises an injector 12 and a monitor assembly 20. The injector 12 comprises a syringe 14 and a biasing device (not shown) that provides a driving force for a plunger 16 through the syringe 14 as illustrated by the directional arrow in FIG. 1. The biasing device may comprise a spring or a frictional engagement between moving parts to regulate relative movement between parts. The frictional engagement may be disposed on or occur at any moving part of the injector 12 in keeping with the object of the present disclosure. In addition to the plunger 16 being disposed on a proximal end of the syringe, the syringe 14 has a needle or another delivery mechanism (not shown) disposed at a distal end of the syringe 14. The biasing device contacts a surface of the plunger 16 opposite the needle and applies a force to the plunger 16, urging the plunger 16 to move in the direction of the needle. In an embodiment of the present disclosure, the biasing device comprises a compression spring (not shown), but other structures have been contemplated, including, for example, a pneumatic and/or telescopic actuator. During an injection sequence, the plunger 16 is moved through the syringe 14 towards the needle, dispelling any contents disposed within the syringe 14 through the needle. In an exemplary embodiment, the syringe 14 is filled with a medication, but can also contain other materials, such as, for example, vitamins, therapeutic substances, diagnostic substances, inert substances (e.g., saline), and/or other infused agents suitable for syringe based administration.

In one embodiment, the injector 12 further comprises a housing 18 adjacent to the syringe 14. The housing 18 provides space for components of the device 10, such as, for example, an electronic storage device 19 may be disposed within the housing 18 to allow for the easy recording and retrieval of data generated by the control unit, as will be discussed. Advantageously, the housing 18 provides a handling device for a patient or medical professional during use.

In an illustrative embodiment depicted in FIG. 1, a monitor assembly 20 is provided. The monitor assembly 20 allows the device 10 to both monitor and control the position of the plunger 16 within the syringe 14, thereby providing data on the progress of the injection. The monitor assembly 20 comprises a resistance unit 21, a gear 22, and a control unit 23. In an exemplary embodiment, the gear 22 is ring-shaped. It has a plurality of teeth 25 on its periphery and is capable of rotating about a central axis 38, located at the center of gear 22. The gear 22 is connected to the plunger 16 so that when the plunger 16 moves in a linear direction through the syringe 14 the gear 22 rotates. The resistance unit 21 translates the linear motion of the plunger 16 to rotational movement of the gear 22.

The resistance unit 21 comprises a soft link 26 and a spool 24. The soft link 26 can have various forms, including a tether, cable, wire, string, tape, filament, or the like, in keeping with the present disclosure. Preferably, the soft link 26 is flexible but has a low elasticity so as to allow for a controlled force distribution. The soft link 26 may be comprised of polyester, Kevlar®, silicon, metal, or any other suitable material. The soft link 26 may also be textured, twisted, or have bumps on its surface that act to damping the force distribution through increased friction. The soft link 26 has two ends, one is attached to the plunger 16, and the other is attached to the spool 24. Because the soft link 26 is flexible, its connection to the plunger 16 and spool 24 can occur at various locations within the device 10. This adaptability feature is beneficial over a rigid link because it allows the resistance unit 21 and the control unit 23 to be relocated at different areas of the injector 24. The soft link 26 is wound up onto the spool 24 and is placed under tension by way of the biasing device, which, as discussed, urges the plunger 16 to move through the syringe 14 towards the needle. The spool 24 therefore houses the soft link 26 and rotates as the soft link 26 is unwound from it. The spool 24 is also connected to the gear 22 so that as the tether 26 is unwound from the spool 24 and rotates the spool 24, the gear 22 rotates as well. In one embodiment, there are a plurality of soft links 26, each operating to regulate linear movement of the plunger 16 and to translate said movement into rotation of the gear 22. In one embodiment, one end of the soft link 26 is attached to an elevator 28 instead of the plunger 16, but because the elevator mates with the plunger 16, the resistance unit 21 does not operate any differently which mates with the plunger. In another embodiment, the resistance unit 21 may include a screw thread engagement or cam follower instead of the soft link 26 configuration. In the screw thread embodiment, the plunger 16 and an inner surface of the syringe 14 may include cooperating threads that translate rotational movement into vertical displacement. In this embodiment, as the plunger 16 rotates and is vertically displaced, the control unit 23 rotates, thereby generating information on the injection progress. One or more ball bearings can be positioned within the threads to dampen and regulate the rotation of the member upon which the threads are disposed. So long as the resistance unit 21 regulates the displacement of the plunger 16, it can assume various configurations in keeping with the present disclosure.

The control unit 23 monitors, records, and communicates the position of the gear 22 as it rotates. Because of the relationship between the gear 22 and the plunger 16, tracking the position of the gear 22 provides information on the position of the plunger 16, a function of the injection progress. In an illustrative embodiment, the control unit 23 comprises an encoder configured to convert information regarding movement of the gear into useful data. In particular, the data can include information on the progress of the injection throughout the injection sequence, the rate of injection, and the detection of an inadvertent stoppage and an alert of the same. Regarding the latter, traditional, purely mechanical large injectors present challenges in detecting inadvertent injection stoppages because the rate of injection is slow. Because of this, injection stoppages are difficult to detect. Thus, a substantial amount of time may pass before it is evident that the injection is not being properly performed. However, the present disclosure addresses this problem by allowing for precise, accurate measuring of the movement of the gear 22, i.e., the displacement of the plunger 16. And if movement of the plunger 16 is obstructed, the control unit can immediately provide a signal that the injection is being prohibited. In this way, the device 10 can provide a signal or alarm that the injection is being obstructed so that re-application of the injector 12 can be made without delay. By monitoring the movement of the gear 22 and displacement of the control unit 23, precise information on the injection process can be generated. Further, displacement of the control unit 23 also allows for the monitoring and administration of various injection patterns or profiles. For instance, some treatments may requires a smooth, regulated injection, while others call for a pulsatile, spiked, or ramped-up injection rate. The ability to control the rate of injection therefore creates a variety of injection profiles for various treatment regimens. The ability to monitor and/or control the injection profile may also help to optimize a drug injection in light of the physical characteristics of the injection site, e.g., tissue elasticity or injection depth.

Figure 3:
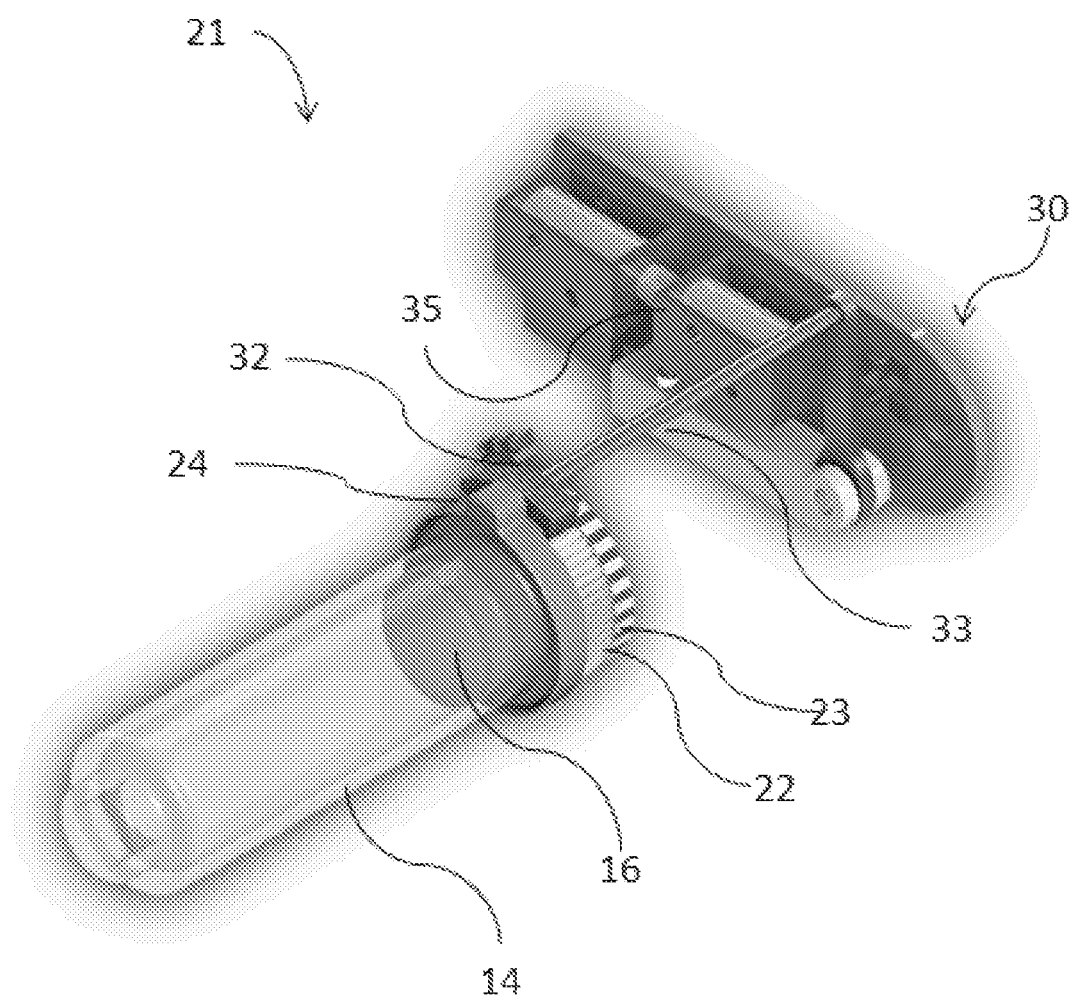
FIG. 3 depicts an exemplary resistance unit including a linkage assembly.
Figure 4:
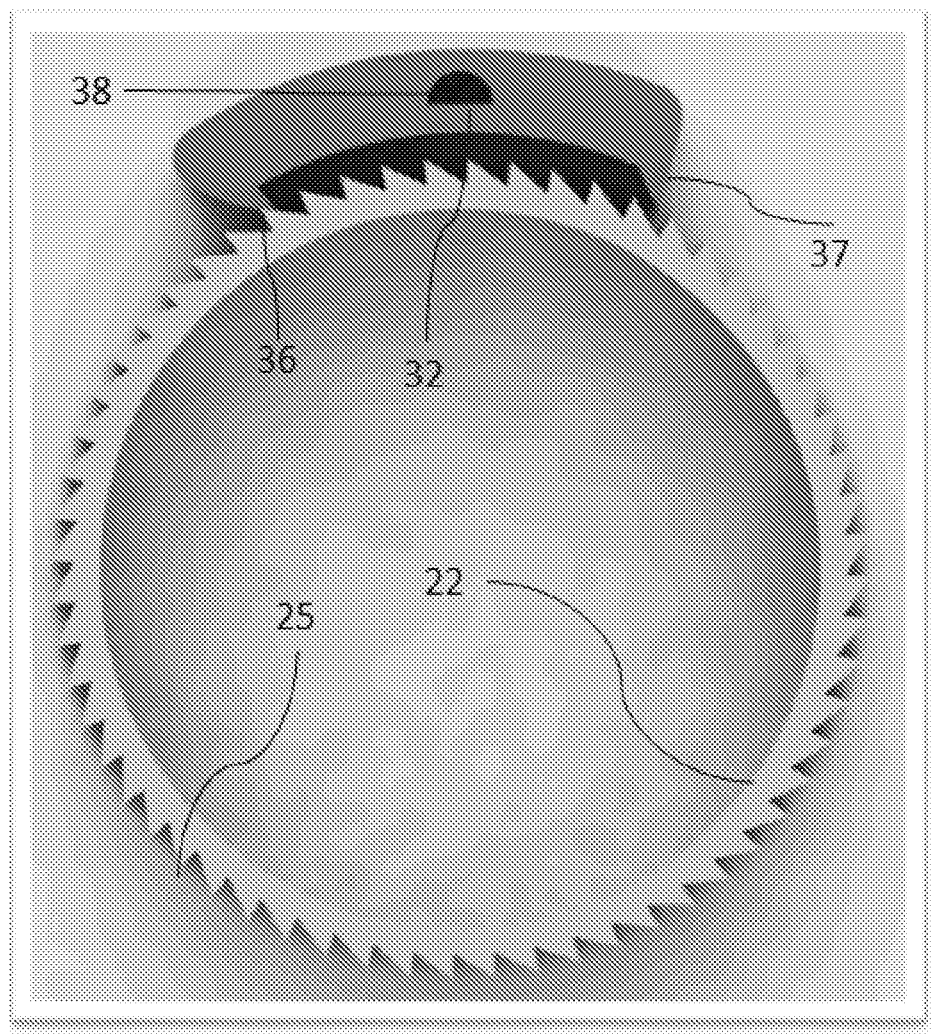
FIG. 4 depicts an exemplary embodiment of a gear and pawl.

In an exemplary embodiment of the disclosure, the resistance device 10 includes a linkage assembly 30. The linkage assembly 30 comprises a pawl 32, a link 33, and an activator 35, depicted in FIG. 3. The pawl 32 is connected to the activator 35 via the link 33. The link 33 provides a fixed axis 38 upon which the pawl 32 rotates. As the activator moves the link 33, the pawl 32 rocks on the fixed axis 38. Although the pawl 32 is depicted having an arcuate shape, other shapes are contemplated in accordance with the present disclosure. The pawl 32 has at least one protrusion 36 disposed on a distal end thereof. The protrusion contacts the teeth 25 of the gear 22 to prevent the gear from rotating freely. In this way, the linkage assembly 30 controls both the rotation of the gear 22 and movement of the plunger 16. As depicted in FIG. 4, in one embodiment, the pawl 32 has a second protrusion 37 opposite the at least one protrusion 36. As the pawl pivots about the fixed axis formed by the link 33, the at least one protrusion 36 and the second protrusion 37 alternatively engage the teeth 25 of the gear 22. As the pawl 32 rocks on its axis 38, the gear 22 is permitted to rotate incrementally. By moving the link 33, the activator 35 causes the pawl 32 to rotate. In this way, the linkage assembly 30 controls the rate of injection, thereby providing a therapeutic benefit under certain conditions. The pawl 32 pivots about an axis, to generate a rocking movement. In an alternate embodiment, the pawl 32 and gear 22 configuration may be replaced by a cam and cam follower in keeping with the present disclosure. In one embodiment, the activator 35 comprises a solenoid that, when activated, moves displacing the link 33, causing the pawl to rotate about the fixed axis 38. Though the illustrative embodiment in FIG. 3 utilizes a solenoid actuator, other activators have been contemplated in keeping with present disclosure, including, for example, various electronic and/or mechanical activators. The activator 35 may also comprise a purely mechanical spring-based, pneumatic, cam, or gear system, in keeping with the present disclosure. The activator 35 can be controlled by the control unit 23. Thus, precise dosing through the entire injection process is possible, thereby eliminating the need for additional monitoring equipment; particularly, when partial or sequential dosing is required.

Further, the control unit 23 is configured for sending data to a separate device (wirelessly or otherwise) where it can be monitored and used to maximize its utility. For example, the wireless device can be programmed to have smart features that track injection progress, control the rate of injection, provide occlusion or obstruction alarms, and provide precise dosing for partial or sequential injections. The control unit 23 is further configured to provide useful information regarding a patient's injection schedule, sending a notification that the patient is due for an injection or that an injection is past-due. The control unit's 23 monitoring of the gear 22 position can be translated into many useful data points, including, for example, the providing precise dosing for a patient, and doing so at a controlled rate. This is particularly useful when a medication's viscosity requires a relatively slow, measured administration. Further, information from the control unit 23 may also be used to generate an injection profile regarding a particular patient or type of injection (e.g., controlled, spiked, ramped, pulsatile, etc.), which is useful for certain treatment regimens.

The control unit 23 may also include a plurality of sensors such as, for example, an accelerometer or a thermistor, thereby generating useful information about the position of the injector 21 during use and the temperature of the drug being administered.

In another embodiment, the resistance unit 21 and control unit 23 are disposed in a manual injector.

In the illustrated embodiments, the device 10 is compact and capable of being used as an add-on feature to existing devices, but it is also contemplated as being made integral with large-volume injectors. The small foot print made by the device 10 gives it broad application in large injector devices and infusion platforms.

While the foregoing drawings and descriptions set forth functional aspects of the disclosed systems, no particular arrangement of these functional aspects should be inferred from these descriptions unless explicitly stated or otherwise clear from the context. Similarly, it will be appreciated that the various steps identified and described above may be varied, and that the order of steps may be adapted to particular applications of the techniques disclosed herein. All such variations and modifications are intended to fall within the scope of this disclosure. As such, the depiction and/or description of an order for various steps should not be understood to require a particular order of execution for those steps, unless required by a particular application, or explicitly stated or otherwise clear from the context.

Further, while embodiments of the present disclosure have been disclosed in connection with the preferred embodiments shown and described in detail, various modifications and improvements thereon will become readily apparent to those skilled in the art. Accordingly, the spirit and scope of the present disclosure is not to be limited by the foregoing examples, but is to be understood in the broadest sense allowable by law.

What is claimed is:

1. A device for monitoring an injection sequence of an injector, the device comprising:
   an injector comprising:
   a syringe having a plunger at a proximal end thereof;
   a biasing device configured to urge the plunger to move towards a distal end of the syringe;
   a monitor assembly connected to the injector, the monitor assembly comprising:
   a resistance unit configured to resist movement of the plunger by the biasing device;
   a gear connected to the plunger by the resistance unit; and
   a control unit configured to monitor the position of the gear; and
   wherein linear movement of the plunger causes the gear to rotate, such that the control unit generates information on the position of the plunger;
   wherein the resistance unit comprises a linkage assembly configured to control the rate of injection, the linkage assembly comprising:
      a pawl having at least one projection on an inner surface, wherein the at least one projection is configured to contact a tooth of the gear to prevent rotation of the gear;
      a link connecting the pawl to an activator, wherein movement of the link causes the pawl to pivot; and
      wherein the activator is configured to move the link, thereby pivoting the pawl and allowing the gear to rotate.

2. The device of claim 1, wherein the resistance unit comprises a spool and a tether, wherein the spool and tether cooperate to translate the linear movement of the plunger into rotation of the gear.

3. The device of claim 2, wherein the tether comprises a first end and a second end, wherein the first end is connected to the plunger, the second end is connected to the spool, and the tether is wound onto the spool.

4. The device of claim 3, wherein the spool is connected to the gear so that rotation of the spool controls the rotation of the gear.

5. The device of claim 4, wherein the linear movement of the plunger towards the distal end of the syringe causes the tether to unwind and the spool to rotate, which, in turn, rotates the gear.

6. The device of claim 1, wherein
   the pawl pivots about a fixed point.

7. The device of claim 1, wherein the control unit is further configured to control the activator to regulate the rate of injection.

8. The device of claim 1, wherein the biasing device comprises a compression spring.

9. The device of claim 1, wherein the control unit comprises an encoder configured to send information to a separate device.

10. The device of claim 9, wherein the information comprises data on at least one of the progress of the injection, the rate of injection, the detection of an occlusion, the detection of an obstruction, an alert regarding the injection, or a reminder to perform the injection.

11. An injector configured to regulate and monitor an injection sequence, the injector comprising:
    an injector assembly comprising:
    a syringe having a plunger at a proximal end thereof;
    a biasing device configured to urge the plunger to move towards a distal end of the syringe;
    a monitor assembly connected to the injector, the monitor assembly comprising:
    a resistance unit configured to resist movement of the plunger by the biasing device;
    a gear connected to the plunger by the resistance unit; and
    a control unit configured to monitor the position and regulate the rotation of the gear; and
    wherein linear movement of the plunger causes the gear to rotate, such that the control unit generates information on the position of the plunger;
    wherein the resistance unit comprises a linkage assembly configured to control the rate of injection, the linkage assembly comprising:
       a pawl having at least one projection on an inner surface, wherein the at least one projection is configured to contact a tooth of the gear to prevent rotation of the gear;
       a link connecting the pawl to an activator, wherein movement of the link causes the pawl to pivot; and
       wherein the activator is configured to move the link, thereby pivoting the pawl and allowing the gear to rotate.

12. The injector of claim 11, wherein the resistance unit comprises a spool and a tether, wherein the spool and tether cooperate to translate the linear movement of the plunger into rotation of the gear.

13. The injector of claim 12, wherein the tether comprises a first end and a second end, wherein the first end is connected to the plunger, the second end is connected to the spool, and the tether is wound onto the spool.

14. The injector of claim 13, wherein the spool is connected to the gear so that rotation of the spool controls the rotation of the gear.

15. The injector of claim 14, wherein the linear movement of the plunger towards the distal end of the syringe causes the tether to unwind and the spool to rotate, which, in turn, rotates the gear.

16. The injector of claim 11, wherein
    the pawl pivots about a fixed point.

17. The injector of claim 11, wherein the control unit is further configured to control the activator to regulate the rate of injection.

18. The injector of claim 11, wherein the biasing device comprises a compression spring.

19. The injector of claim 11, wherein the control unit comprises an encoder configured to send information to a separate device.

20. The injector of claim 19, wherein the information comprises data on at least one of the progress of the injection, the rate of injection, the detection of an occlusion, the detection of an obstruction, an alert regarding the injection, or a reminder to perform the injection.

* * * * *